United States Patent [19]

Berger et al.

[11] 4,192,809

[45] Mar. 11, 1980

[54] CERTAIN 8-HALODIBENZOFURAN-3-ALKANOLS

[75] Inventors: Leo Berger, Montclair; Robert A. Schmidt, Wallington, both of N.J.

[73] Assignee: Hoffmann-La Roche Inc., Nutley, N.J.

[21] Appl. No.: 894,282

[22] Filed: Apr. 7, 1978

Related U.S. Application Data

[60] Division of Ser. No. 763,446, Jan. 27, 1977, Pat. No. 4,097,497, which is a division of Ser. No. 548,658, Feb. 10, 1975, Pat. No. 4,022,805, which is a continuation-in-part of Ser. No. 448,853, Mar. 7, 1974, abandoned.

[51] Int. Cl.² .................................................. C07D 307/91
[52] U.S. Cl. ............................................... 260/346.71
[58] Field of Search ................................ 260/346.71

[56] References Cited

U.S. PATENT DOCUMENTS 3,897,453  7/1975  Gante et al. .................. 260/346.71

FOREIGN PATENT DOCUMENTS 445743  6/1970  Australia .
532629  2/1973  Switzerland .

OTHER PUBLICATIONS

J. Indian Chem. Soc. 33 (1956), pp. 447–454

Primary Examiner—Alan L. Rotman
Assistant Examiner—Bernard Dentz
Attorney, Agent, or Firm—Jon S. Saxe; George M. Gould; William G. Isgro

[57] ABSTRACT

Dibenzofurans of the formula

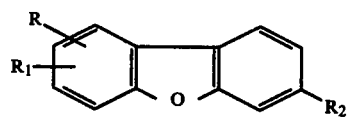

I wherein R, $R_1$ and $R_2$ are as hereinafter described, prepared, inter alia, from the correspondingly substituted phenol and haloketocyclohexane are described. The dibenzofurans of the invention are useful antiinflammatory, analgesic and anti-rheumatic agents.

5 Claims, No Drawings

CERTAIN 8-HALODIBENZOFURAN-3-ALKANOLS

This is a division, of application Ser. No. 763,446, filed Jan. 27, 1977, now U.S. Pat. No. 4,097,497, patented June 27, 1978, which in turn is a division of U.S. patent application Ser. No. 548,658, filed Feb. 10, 1975, now U.S. Pat. No. 4,022,805, patented May 10, 1977, which in turn is a continuation-in-part of U.S. patent application Ser. No. 448,853, filed Mar. 7, 1974, now abandoned.

BRIEF SUMMARY OF THE INVENTION

The invention relates to compounds of the formula

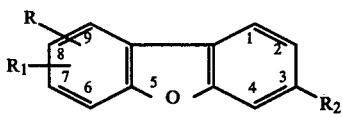

wherein R is hydrogen, halogen, hydroxy, cyano, lower alkyl, hydroxy-lower alkyl, lower alkoxy, acyl, benzyloxy, lower alkylthio, trifluoromethyl, carboxy, carbo-lower alkoxy, nitro, amino, mono-lower alkylamino, di-lower alkylamino, sulfamoyl, di-lower alkylsulfamoyl or difluoromethylsulfonyl; $R_1$ is halogen, cyano, lower alkyl, hydroxy-lower alkyl, lower alkoxy, acyl, acylamido, benzyloxy, lower alkylthio, trifluoromethyl, hydroxy, carboxy, carbo-lower alkoxy, nitro, amino, mono-lower alkylamino, di-lower alkylamino, sulfamoyl, di-lower alkylsulfamoyl or difluoromethylsulfonyl, or R taken together with an adjacent $R_1$ is also lower alkylenedioxy; $R_2$ is

wherein A is cyano, hydroxy, lower alkoxy, amino-lower alkoxy, mono-lower alkylamino-lower alkoxy or di-lower alkylamino-lower alkoxy, X and Y, independently, are hydrogen or lower alkyl, and m is 1 to 7, or $R_2$ is

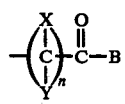

wherein B is hydroxy, carboxy, lower alkoxy, amino, hydroxyamino, mono-lower alkylamino, di-lower alkylamino, amino-lower alkoxy, mono-lower alkylamino-lower alkoxy or di-lower alkylamino-lower alkoxy, Y and X, independently, are hydrogen or lower alkyl; and n is 1 to 7;
when X and Y are different, their enantiomers; when R or $R_1$ is carboxy and/or when B is hydroxy or carboxy, salts thereof with pharmaceutically acceptable bases; and when R or $R_1$ is amino, mono-lower alkylamino or di-lower alkylamino, and/or when B or A is amino-lower alkoxy, mono-lower alkylamino-lower alkoxy or di-lower alkylamino-lower alkoxy, addition salts thereof with pharmaceutically acceptable acids. The dibenzofurans of formula I are useful as anti-inflammatory, analgesic and anti-rheumatic agents.

DETAILED DESCRIPTION OF THE INVENTION

As used herein, the term "lower alkyl" denotes a straight or branched chain hydrocarbon group containing 1-7 carbon atoms, for example, methyl, ethyl, propyl, isopropyl, butyl, isobutyl, tertiary butyl, neopentyl, pentyl, heptyl, and the like. The term "lower alkoxy" denotes an alkyl ether group in which the alkyl group is as described above, for example, methoxy, ethoxy, propoxy, isopropoxy, butoxy, pentoxy and the like. The term "lower alkylthio" denotes an alkyl thioether group in which the alkyl group is as described above, for example, methylthio, ethylthio, propylthio, isopropylthio, butylthio, pentylthio and the like. The term "halogen" denotes all the halogens, that is, bromine, chlorine, fluorine and iodine; bromine and chlorine are preferred. The term "acyl" denotes an "alkanoyl" group derived from an aliphatic carboxylic acid of 1 to 7 carbon atoms, for example, formyl, acetyl, propionyl, and the like, and an "aroyl" group derived from an aromatic carboxylic acid, such as benzoyl and the like. The term "lower alkylene" denotes a straight or branched chain alkylene of 1-7 carbon atoms, for example, methylene, ethylene, propylene, butylene, methylmethylene and the like. The term "lower alkylenedioxy" preferably denotes methylenedioxy and the like.

Exemplary of mono-lower alkylamino are methylamino, ethylamino and the like. Exemplary of di-lower alkylamino are dimethylamino, diethylamino and the like. Exemplary of amino-lower alkoxy are aminomethoxy, aminoethoxy and the like. Exemplary of mono-lower alkylamino-lower alkoxy are methylamino-methoxy ethylaminoethoxy and the like. Exemplary of di-lower alkylamino-lower alkoxy are dimethylaminomethoxy, diethylaminoethoxy and the like. Exemplary of dilower alkylsulfamoyl are dimethylsulfamoyl, diethylsulfamoyl and the like.

The invention relates to compounds of the formula

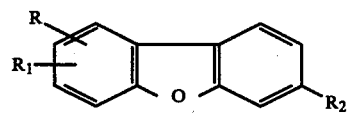

wherein R is hydrogen, halogen, hydroxy, cyano, lower alkyl, hydroxy-lower alkyl, lower alkoxy, acyl, benzyloxy, lower alkylthio, trifluoromethyl, carboxy, carbo-lower alkoxy, nitro, amino, mono-lower alkylamino, di-lower alkylamino, sulfamoyl, di-lower alkylsulfamoyl or difluoromethylsulfonyl; $R_1$ is halogen, cyano, lower alkyl, hydroxy-lower alkyl, lower alkoxy, acyl, acylamido, benzyloxy, lower alkylthio, trifluoromethyl, hydroxy, carboxy, carbo-lower alkoxy, nitro, amino, mono-lower alkylamino, di-lower alkylamino, sulfamoyl, di-lower alkylsulfamoyl or difluoromethylsulfonyl, or R taken together with an adjacent $R_1$ is also lower alkylenedioxy; $R_2$ is

wherein A is cyano, hydroxy, lower alkoxy, amino-lower alkoxy, mono-lower alkylamino-lower alkoxy or di-lower alkylamino-lower alkoxy, Y and X, independently, are hydrogen or lower alkyl, and m is 1 to 7, or R₂ is

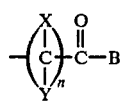

wherein B is hydroxy, carboxy, lower alkoxy, amino, hydroxyamino, mono-lower alkylamino, di-lower alkylamino, amino-lower alkoxy, mono-lower alkylamino-lower alkoxy or di-lower alkylamino-lower alkoxy; Y and X, independently, are hydrogen or lower alkyl; and n is 1 to 7; and when X and Y are different, their enantiomers; when R or R₁ is carboxy and/or when B is hydroxy or carboxy, salts thereof with pharmaceutically acceptable bases; and when R or R₁ is amino, mono-lower alkylamino or di-lower alkylamino, and/or when B or A is amino-lower alkoxy, mono-lower alkylamino-lower alkoxy or di-lower alkylamino-lower alkoxy, addition salts thereof with pharmaceutically acceptable acids.

Preferred dibenzofurans of the invention are those characterized by the formulas

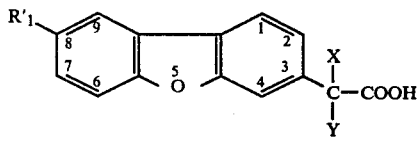

and

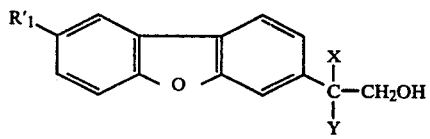

wherein R'₁ is halogen, lower alkyl or lower alkoxy, preferably R'₁ is halogen or lower alkoxy, and most preferably R'₁ is halogen; and X and y are as previously described, their enantiomers when X and Y are different, and salts of the compounds of formula I' with pharmaceutically acceptable bases. Preferably, in formula I, m is 2 and n is 1.

Preferred compounds of formula I are:
racemic 8-chloro-α-methyl-dibenzofuran-3-acetic acid;
(+)8-chloro-α-methyl-dibenzofuran-3-acetic acid;
(−)8-chloro-α-methyl-dibenzofuran-3-acetic acid;
racemic 2-(8-chloro-3-dibenzofuranyl)propanol;
2-(8-chloro-3-dibenzofuranyl)ethanol;
8-chloro-dibenzofuran-3-acetic acid;
8-chloro-α-methyl-dibenzofuran-3-acetamide;
8-chloro-α-methyl-3-dibenzofuran acetic acid-2-dimethylaminoethyl ester;
8-fluoro-α-methyldibenzofuran-3-acetic acid.

Exemplary of compounds of this invention corresponding to formula I are:
8-chloro-dibenzofuran-3-acetic acid;
8-chloro-dibenzofuran-3-acetic acid ethyl ester;
8-methoxy-dibenzofuran-3-acetic acid;
8-nitro-dibenzofuran-3-acetic acid;
7-methoxy-dibenzofuran-3-acetic acid;
7-chloro-dibenzofuran-3-acetic acid;
8-methyl-dibenzofuran-3-acetic acid;
6-chloro-dibenzofuran-3-acetic acid;
8,9-dichloro-dibenzofuran-3-acetic acid;
α-methyl-dibenzofuran-3-acetic acid;
8-carbethoxy-dibenzofuran-3-acetic acid;
7-methyl-dibenzofuran-3-acetic acid;
7,8-dichloro-dibenzofuran-3-acetic acid;
8-chloro-9-methyl-dibenzofuran-3-acetic acid;
8-difluoromethylsulfonyl-dibenzofuran-3-acetic acid;
(+)8-chloro-α-methyl-dibenzofuran-3-acetic acid (−)-α-methylbenzyl amine salt;
racemic 2-(8-chloro-3-dibenzofuranyl)propanol methyl ether;
8-chloro-7-methyl-dibenzofuran-3-acetic acid;
8-sulfamoyl-dibenzofuran-3-acetic acid;
8-benzoyl-dibenzofuran-3-acetic acid;
8-fluoro-dibenzofuran-3-acetic acid;
8-trifluoromethyl-dibenzofuran-3-acetic acid;
6,7-dichloro-dibenzofuran-3-acetic acid;
9-chloro-8-sulfamyl-dibenzofuran-3-acetic acid;
8-methylthio-dibenzofuran-3-acetic acid;
8-ethyl-dibenzofuran-3-acetic acid;
8-chloro-dibenzofuran-3-acetic acid dimethylaminoethyl ester;
8-methyl-dibenzofuran-3-acetic acid ethyl ester;
8-dimethylsulfamoyl-dibenzofuran-3-acetic acid;
8-carboxy-dibenzofuran-3-acetic acid;
8-iodo-dibenzofuran-3-acetic acid;
8-chloro-N,N-dimethyl-dibenzofuran-3-acetamide;
8-cyano-dibenzofuran-3-acetic acid;
8-acetyl-dibenzofuran-3-acetic acid;
8-chloro-dibenzofuran-3-acetic acid dimethylaminoethyl ester hydrochloride;
8-benzyloxy-dibenzofuran-3-acetic acid;
7,8-methylenedioxy-dibenzofuran-3-acetic acid;
8-hydroxy-dibenzofuran-3-acetic acid;
7-chloro-dibenzofuran-3-acetic acid ethyl ester;
9-chloro-dibenzofuran-3-acetic acid ethyl ester;
8-bromo-dibenzofuran-3-acetic acid ethyl ester;
8-acetamido-dibenzofuran-3-acetic acid ethyl ester;
8-chloro-dibenzofuran-3-propionic acid ethyl ester;
8-chloro-α,α-dimethyl-dibenzofuran-3-acetic acid ethyl ester;
8-chloro-dibenzofuran-3-acetamide;
8-trifluoromethyl-dibenzofuran-3-acetic acid ethyl ester;
6,7-dichloro-dibenzofuran-3-acetic acid ethyl ester;
8,9-dichloro-dibenzofuran-3-acetic acid ethyl ester;
8-methylthio-dibenzofuran-3-acetic acid ethyl ester;
8-carbethoxy-dibenzofuran-3-acetic acid ethyl ester;
8-fluoro-dibenzofuran-3-acetic acid ethyl ester;
α-methyl-dibenzofuran-3-acetic acid ethyl ester;
8-N,N-dimethylsulfamoyl-dibenzofuran-3-acetic acid ethyl ester;
8-cyano-dibenzofuran-3-acetic acid ethyl ester;
7,8-dichloro-dibenzofuran-3-acetic acid ethyl ester;
8-nitro-dibenzofuran-3-acetic acid ethyl ester;
and the like.

The preparation of the compounds of formula I is exemplified as hereinafter described.

More particularly, a halobenzene of the formula

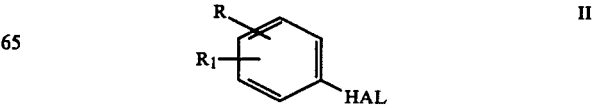

wherein HAL is halogen, for example, chlorine, fluorine, bromine and iodine, preferred is fluorine; and R, $R_1$ and $R_2$ are as previously described,
is reacted with an oxime of the formula

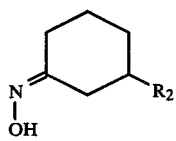

wherein $R_2$ is as previously described,
to yield an O-phenyl oxime of the formula

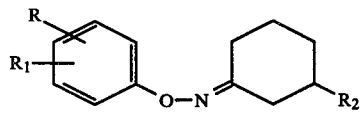

wherein R, $R_1$ and $R_2$ are as previously described,
in a polar solvent, such as dimethylsulfoxide, dimethylformamide, or hexamethylphosphoric triamide. The reaction temperature is not critical. Preferably the reaction is carried out at a temperature in the range of from about room temperature to about the reflux temperature of the reaction mixture. The molar ratio of the reactants is not critical. Preferably, they are reacted in a 1:1 molar ratio.

The oxime of formula IV is converted to the compound of the formula

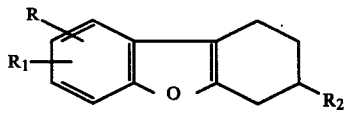

wherein R, $R_1$ and $R_2$ are as previously described, utilizing, for example, an acidic catalyst such as an organic, inorganic or Lewis acid, exemplary of which are hydrochloric acid, sulfuric acid, phosphoric acid, zinc chloride, copper chloride, boron trifluoride and the like, and various combinations thereof. Conveniently, the reaction can be carried out in a polar solvent such as an alkanol, for example, methanol, ethanol, propanol, and the like, water or a hydrocarbon such as benzene, toluene and the like. The reaction temperature is not critical. Preferably, the reaction is carried out at a temperature in the range of from about room temperature to about the reflux temperature of the reaction mixture. The separation of the desired compound of formula V from the reaction mixture can be effected utilizing known techniques such as, for example, filtration, crystallization, distillation and the like.

A nitro group present in the compound of formula V can be converted to an amino group utilizing known procedures, for example, by catalytic reduction. An amino group can be converted to a diazonium salt utilizing known procedures, for example, by reaction with sodium nitrate and a mineral acid such as a hydrohalic acid. A diazonium group can then be replaced by a halogen, cyano, hydroxy, lower alkoxy or hydrogen utilizing known procedures, for example, by mixing a diazonium salt solution with, for example, a cuprous halide, cuprous cyanide, water, an alkanol or a reducing agent such as hypophosphorous acid, respectively, at room temperature or occasionally at elevated temperatures.

The compounds of formula I can also be prepared by alkylating a compound of the formula

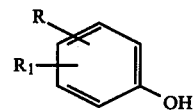

wherein R and $R_1$ are as previously described,
with the corresponding haloketocycloalkane compound of the formula

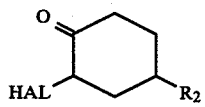

wherein HAL and $R_2$ are as previously described,
to yield a compound of the formula

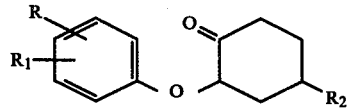

wherein R, $R_1$ and $R_2$ are as previously described.
The reaction is conveniently carried out in a non-polar solvent, for example, a hydrocarbon, such as benzene, toluene and the like, or a polar solvent, such as dimethylsulfoxide, dimethylformamide, hexamethylphosphoric triamide, and the like. The reaction temperature is not critical. Preferably, the reaction is carried out at a temperature in the range of from about room temperature to about the reflux temperature of the reaction mixture. The molar ratio of the reactants is not critical. Preferably, they are reacted at a 1:1 molar ratio.

A compound of formula VIII is converted to a compound of formula V by thermal cyclization or by utilizing a cyclizing agent, such as polyphosphoric acid, and the like. Preferably, the reaction is carried out at a temperature in the range of from about $-20°$ to about $120°$. The reaction can be conveniently carried out with or without a solvent. Exemplary of convenient solvents are acetic acid and the like.

An ester of formula I can be converted to the corresponding acid, i.e., the compounds of formula I wherein B is hydroxy, by saponification according to known procedures, for example, by reaction with an alkali metal hydroxide such as sodium hydroxide, potassium hydroxide and the like, and subsequent treatment with a mineral acid, for example, a hydrohalic acid such as hydrochloric acid and the like.

The separation of the desired compound of formula I and its corresponding acid from the reaction mixture can be effected utilizing known techniques such as, for example, filtration, crystallization, distillation and the like.

Furthermore, a salt of an acid of formula I, i.e., a salt of compounds of formula I wherein B is hydroxy, can be converted to a compound of formula I wherein B is amino-lower alkyl, mono-lower alkylamino-lower alkyl or di-lower alkylamino-lower alkyl by known procedures. For example, a salt of an acid of formula I is reacted with an amino-lower alkyl halide, mono-lower alkylamino-lower alkyl halide or di-lower alkylamino-lower alkyl halide, exemplary of which are aminoethyl chloride, methylamino-ethyl bromide, diethylaminomethyl chloride and the like, to yield the desired end product. The temperature at which the reaction is effected is not critical; conveniently, the reaction is carried out at a temperature in the range of from about room temperature and about the reflux temperature of the reaction mixture. Conveniently, the reaction can be carried out in a polar solvent, such as dimethylformamide, dimethylsulfoxide or the like. The molar ratio of reactants is not critical. Preferably, the reactants are utilized in a 1:1 molar ratio.

The starting materials of formula II are known compounds or can be prepared in an analogous manner to known compounds. Exemplary of such compounds are:
4-fluoronitrobenzene;
4-fluorocyanobenzene;
4-fluoroacetophenone; and the like.

The starting materials of formula III are known compounds or can be prepared in an analogous manner to known compounds. Exemplary of such compounds are:
3-oxyiminocyclohexaneacetic acid methyl ester;
3-oxyiminocyclohexaneacetic acid ethyl ester;
3-oxyiminocyclohexaneacetic acid propyl ester;
3-oxyiminocyclohexaneacetic acid butyl ester; and the like.

The intermediates of formula IV are novel compounds. Exemplary of such compounds are:
3-(4-nitrophenoxyimino)cyclohexaneacetic acid and methyl ester thereof;
3-(2-nitrophenoxyimino)cyclohexaneacetic acid and methyl ester thereof;
3-(4-cyanophenoxyimino)cyclohexaneacetic acid;
3-(2-trifluoromethylphenoxyimino)cyclohexaneacetic acid; and the like.

The starting materials of formula VI are known compounds or can be prepared in an analogous manner to known compounds. Exemplary of such compounds are:
4-chlorophenol;
5-chlorophenol;
4-nitrophenol;
p-cresol.

The starting materials of formula VII can be prepared by halogenating a compound of the formula

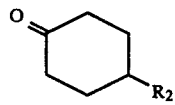

IX wherein $R_2$ is as previously described;
to yield a compound of the formula

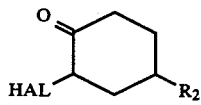

VII wherein HAL and $R_2$ are as previously described.

The compounds of formula IX are known compounds or can be prepared in an analogous manner to known compounds.

The halogenation is effected utilizing known procedures, for example, utilizing a halogen such as bromine in ether, at a temperature of $-10°$ C. Exemplary of such compounds are:
3-bromo-4-ketocyclohexaneacetic acid;
3-bromo-4-ketocyclohexaneacetic acid ethyl ester; and the like.

Exemplary of the intermediates of formula VIII are:
3-(4-chloro-phenoxy)-4-oxocyclohexaneacetic acid and ethyl ester thereof;
3-(4-bromo-phenoxy)-4-oxocyclohexaneacetic acid and methyl ester thereof; and the like.

The 1,2-dihydro-3(4H)-dibenzofuran of formula V is then aromatized to the corresponding compound of formula I.

The compound of formula V is converted to the compound of formula I utilizing an aromatizing agent, for example, p-chloranil, o-chloranil, 2,3-dichloro-5,6-dicyanobenzoquinone (DDQ), sulfur, palladium on carbon, lead oxide, and the like, in the presence of a solvent, for example, xylene, benzene, toluene, quinoline, dimethylsulfoxide (DMSO), dimethylformamide (DMF). The aromatization is carried out at a temperature in the range of from about room temperature to about the reflux temperature of the reaction mixture; preferably, it is carried out at the reflux temperature of the reaction mixture. The compound of formula I can be separated from the reaction mixture by known procedures, included among which are, for example, filtration, crystallization, distillation and the like.

Alternatively, an acid of formula I, prepared from the corresponding ketone of formula VII, wherein $R_2$ is carboxy, can be converted to the corresponding ester by known procedures. For instance, (a) an acid of formula I can be reacted with an alkanol such as methanol, ethanol, propanol or the like, at a temperature in the range of from about room temperature to the reflux temperature of the reaction mixture, or (b) an alkali metal salt of an acid of formula I, such as the sodium salt, can be reacted with a substituted or unsubstituted alkyl halide utilizing known reaction conditions, for example, in an inert solvent such as benzene, toluene, dimethylformamide or the like, at a temperature in the range of from about room temperature to the reflux temperature of the reaction mixture.

A compound of formula I, wherein R or $R_1$ is amino, can be converted to the corresponding compound wherein R or $R_1$ is dialkylamino, utilizing known procedures, for example, utilizing hydrogen at a pressure of from about 1 atmosphere to about several atmospheres and a catalyst such as Raney nickel, together with an alkyl aldehyde such as formaldehyde, at a temperature in the range of from about room temperature to about 100°, in a solvent, for example, an alkanol such as methanol, ethanol, or the like.

A compound of formula I, wherein R, $R_1$ or $R_2$ is alkoxyalkyl, can be converted to the corresponding compound, wherein R, $R_1$ or $R_2$ is hydroxyalkyl, by known procedures. For example, a compound of formula I bearing an alkoxy group can be treated with a mineral acid, for example, a hydrohalic acid such as hydrobromic acid, or the like, in a solvent, for example, alkanols such as ethanol, propanol, or the like, at a temperature in the range of from about room temperature to about the reflux temperature of the reaction mixture. The conversion can also be effected utilizing a Lewis acid, such as aluminum tribromide, boron trifluoride, tin tetrachloride or the like, in a solvent such as benzene, toluene, dimethylformamide or the like.

An alcohol of formula I, i.e., an alcohol prepared from the corresponding ketone of formula VII, wherein A is hydroxy, can be converted to the corresponding compound of formula I wherein A is lower alkoxy, amino-lower alkoxy, mono-lower alkylamino-lower alkoxy or di-lower alkylamino-lower alkoxy by known procedures. For example, an alcohol of formula I, wherein A is hydroxy, is treated with an alkali metal such as sodium. The resulting compound is then treated with a halide (X) of the formula RX, wherein R is lower alkyl, amino-lower alkyl, mono-lower alkylamino-lower alkyl or di-lower alkylamino-lower alkyl, utilizing known reaction conditions.

A compound of formula I, wherein B is lower alkoxy, can be de-esterified to the corresponding compound of formula I wherein B is hydroxy, with an alkali hydroxide, such as sodium hydroxide, potassium hydroxide or the like, in the presence of a solvent, for example, an alkanol such as methanol, ethanol or the like. The de-esterification can be carried out at a temperature in the range of from about room temperature to about the reflux temperature of the reaction mixture preferably, it is carried out at the reflux temperature of the reaction mixture. The compound of formula I can be separated from the reaction mixture by known procedures.

An ester of formula I can be converted to the corresponding alcohol, e.g., wherein A is hydroxy or R and/or $R_1$ is carbo-lower alkoxy, by known procedures. For example, an ester of formula I can be treated with a reagent such as lithium aluminum hydride, at a temperature in the range of from about room temperature to the reflux temperature of the reaction mixture. Thereafter, the corresponding alcohol which is formed can be separated by known procedures.

A compound of formula I, wherein $R_1$ is acylamido, can be converted to the corresponding compound of formula I, wherein $R_1$ is amino, by treatment with an inorganic acid, for example, a hydrohalic acid such as hydrochloric acid or the like, utilizing known reaction conditions.

The acids of formula I, i.e., the compounds of formula I, wherein B is hydroxy, and salts of such acids with bases, can be converted to a compound of formula I wherein B is amino-lower alkoxy, mono-lower alkylamino-lower alkoxy or di-lower alkylamino-lower alkoxy by known procedures. For example, a salt of an acid of formula I is reacted with an amino-lower alkyl halide, mono-lower alkylamino-lower alkyl halide or di-lower alkylamino-lower alkyl halide, exemplary of which are aminoethyl chloride, methylamino-ethyl bromide, diethylaminomethyl chloride and the like, to yield the desired end product. The temperature at which the reaction is effected is not critical; conveniently, the reaction is carried out at a temperature in the range of from about room temperature and about the reflux temperature of the reaction mixture. Conveniently, the reaction can be carried out in a polar solvent, such as dimethylformamide, dimethylsulfoxide or the like. The molar ratio of reactants is not critical. Preferably, the reactants are utilized in a 1:1 molar ratio.

The compounds of formula I when R or $R_1$ is amino, mono-lower alkylamino, di-lower alkylamino, and/or when B or A is amino-lower alkoxy, mono-lower alkylamino-lower alkoxy or di-lower alkylamino-lower alkoxy, form addition salts with pharmaceutically acceptable organic or inorganic acids such as hydrohalides, e.g., hydrochloride, hydrobromide, hydroiodide, other mineral acid salts such as sulfate, nitrate, phosphate and the like, alkyl- and mono-arylsulfonates such as ethanesulfonate, toluenesulfonate, benzenesulfonate, or the like, other organic acid salts such as acetate, tartrate, maleate, citrate, benzoate, salicylate, ascorbate and the like.

The compounds of formula I, when R or $R_1$ is carboxy and/or B is hydroxy or carboxy, form salts with pharmaceutically acceptable bases. Exemplary of such bases are alkali metal hydroxides, such as sodium hydroxide, potassium hydroxide, and the like; alkaline earth hydroxides, such as calcium hydroxide, barium hydroxide and the like; sodium alkoxides, such as sodium ethanolate, potassium ethanolate and the like; organic bases such as piperidine, diethanolamine, N-methylglucamine, and the like. Also included are the aluminum salts of the compounds of formula I, as above.

The compounds of formula I, including the salts of those compounds of formula I which form salts with pharmaceutically acceptable bases and acids, possess anti-inflammatory, analogesic and anti-rheumatic activity, and are therefore useful as anti-inflammatory, analgesic and anti-rheumatic agents. The compounds of formula I also exhibit a significantly low incidence of ulcergenic activity, which renders them highly desirable as anti-inflammatory, analgesic and anti-rheumatic agents. Their pharmacologically useful activities are demonstrated in warmblooded animals using standard procedures.

For example, the anti-inflammatory activity is demonstrated in Albino rats of Hart Strain, weighing 125–155 gms. The test animals are given 10 mls. of vehicle[1], which contains the test compound per kg. of body weight. Th animals are treated daily for 5 consecutive days. Three hours after the first treatment, 0.05 ml. of an 0.5% suspension of heat killed dessiccated *Mycobacterium butyricum* in U.S.P. olive oil, which has been steam sterilized for 30 minutes, is injected into the right hind foot of each rat. The paw volume is measured immediately after the injection of the adjuvant and again 96 hours later. The difference is recorded as volume of edema. The paw volume is measured by immersion of the paw into a column of mercury to an ink mark exactly at the level of the lateral malleolus. Percent inhibition is calculated by dividing the average control edema minus the average treatment edema by the average control edema times 100. The percent inhibition is plotted against dose on semi-logarithmic probability paper and the dose required to produce a 30% reduction in edema is estimated therefrom and is expressed as $ED_{30}$.

[1]Hilgar, A. G. and Hummel, D. J.: Endocrine Bioassay Data. No. 1, p. 15, August 1964 (Cancer Chemotherapy National Service Center, N.I.H.)

When 8-chloro-dibenzofuran-3-acetic acid, which has demonstrated an $LD_{50}$ of, for example, 775 mg. p.o. in mice, is utilized as the test substance at a dosage of 0.03 gm. p.o., an anti-inflammatory activity is observed ($ED_{30}=1.6$).

The analgesic activity of the compounds of the invention is demonstrated, for example, employed the method which is a modification of that described by Eddy (1950), Wolfe and MacDonald (1944) and Eddy and Leimbach (1952). The method determines the reaction time of mice dropped onto a hot plate maintained at 55°±0.5° C. Six groups of male mice (5 mice/group) weighing between 20–30 grams are utilized. The initial reaction time of these mice is determined once, and the reaction time of each group is then averaged. The mice are then administered the vehicle and/or the compound to be tested by the oral, intraperitoneal or subcutaneous route. The average reaction time of each group is determined again at 30, 60 and 90 minutes after compound administration and is compared to controls. Reaction time is recorded as percent changes from control All groups are averaged before and after treatment. A combined reaction time average (recorded as percent change of reaction time threshhold from controls) for all three periods is plotted against dose on graph paper, and a curve is drawn. The $ED_{50}$ is read from this curve.

When 8-chloro-dibenzofuran-3-acetic acid, which has demonstrated an $LD_{50}$ of, for example, 775 mg. p.o. in mice, is utilized as the test substance, analgesic activity is observed at an $ED_{50}$ of 74.

The compounds of formula I, their enantiomers and salts thereof as herein described, have effects qualitatively similar to those of phenylbutazone and indomethacin, known for their therapeutic uses and properties. Thus, the end products of this invention demonstrate a pattern of activity associated with anti-inflammatory agents of known efficacy and safety.

The compounds of formula I, their enantiomers and salts thereof as herein described, can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkylene-glycols, and the like. The pharmaceutical preparations can be employed in a solid form, for example, as tablets, troches, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

Since the compounds of the invention when X and Y in formula I are different possess an asymmetric carbon atom, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture with an optically active resolving agent, for example, an optically active base, such as d-α-methylbenzylamine, which can be reacted with the carboxyl group. The formed diastereomers are separated by selective crystallization and converted to the corresponding optical isomer. Thus, the invention covers the racemates of the compounds of formula I as well as their optically active isomers.

The Examples which follow further illustrate the invention. All temperatures are in degrees Centigrade, unless otherwise mentioned.

EXAMPLE 1

Preparation of 3-bromo-4-oxocyclohexylacetic acid ethyl ester

To a solution of 16 g. of 4-oxocyclohexylacetic acid ethyl ester in 200 ml. of ether, stirred and cooled to −10° C., were added 4.48 ml. of bromine, dropwise. After one-half hour, the ether solution was washed successively with two 100 ml. portions of water, one 100 ml. portion of saturated sodium bicarbonate, and three 100 ml. portions of water. The aqueous layers were extracted with two 100 ml. portions of ether. The organic layers were combined, dried over anhydrous sodium sulfate, and evaporated at reduced pressure to give 23 g. of 3-bromo-4-oxocyclohexylacetic acid ethyl ester as a pale yellow oil.

EXAMPLE 2

Preparation of 3-(4-chlorophenoxy)-4-oxocyclohexylacetic acid ethyl ester

A mixture of 11.2 g. of 4-chlorophenol, 24 g. of anhydrous potassium carbonate, and 45 ml. of dimethylformamide was stirred at 100° C. for 10 minutes. After stirring and cooling for two hours, the mixture was treated dropwise over a period of one hour with a solution of 23 g. of 3-bromo-4-oxocyclohexylacetic acid ethyl ester in 45 ml. of dimethylformamide, heated at 100° C. for 1.25 hours, and finally stirred at room temperature for 64 hours. The solid which formed was removed by filtration and washed with dimethylformamide. The filtrate and washings were combined and concentrated at 40° C. and reduced pressure to give 33 g. of oil. Then, the oil was mixed with 200 ml. of water and extracted with three 200 ml. portions of ether. The organic layers were washed successively with 200 ml. of water, three 100 ml. portions of 1 N sodium hydroxide, three 200 ml. portions of water, dried over anhydrous sodium sulfate, and evaporated to give 23 g. of 3-(4-chlorophenoxy)-4-oxocyclohexylacetic acid ethyl ester as a yellow oil. A portion of the oil was distilled in a rotating Buchi kugelrohr and yielded the ester as a pale yellow oil having a boiling point of 178°/0.55 mm.

EXAMPLE 3

Preparation of 8-chloro-1,2-dihydro-3(4H)-dibenzofuranacetic acid ethyl ester

A mixture of 70 g. of 3-(4-chlorophenoxy)-4-oxocyclohexylacetic acid ethyl ester and 700 g. of polyphosphoric acid was stirred at room temperature for 2.75 hours under an atmosphere of nitrogen, allowed to stand for 1.5 hours and stirred on a steambath for 0.25 hour. The hot, viscous mass which formed was decomposed by pouring onto ice, and the resultant cold mixture was extracted with three 500 ml. portions of ether. The organic layers were washed successively with two 250 ml. portions of water, three 100 ml. portions of 1 N sodium hydroxide and four 100 ml. portions of water and subsequently dried over anhydrous sodium sulfate, charcoal added. The solvent was evaporated to give 56.1 g. of a turbid oil. A portion of this material was distilled to give 17.4 g. of 8-chloro-1,2-dihydro-3(4H)-dibenzofuranacetic acid ethyl ester having a boiling point of 166°-167°/0.03 mm. (99.8% purity by gas chromatography). A sample, distilled in a rotating Buchi kugelrohr had a boiling point of 150°-160°/0.5 mm., crystallized on standing, m.p. 54°-55.5°.

EXAMPLE 4

Preparation of 8-chloro-3-dibenzofuranacetic acid ethyl ester

A mixture of 7.23 g. of 8-chloro-1,2-dihydro-3(4H)-dibenzofuranacetic acid ethyl ester, 11.8 g. of 2,3-dichloro-5,6-dicyano-1,4-benzoquinone and 150 ml. of benzene was stirred at reflux temperature for 18 hours under an atmosphere of nitrogen, and then cooled. The solid was removed by filtration and washed with benzene. The filtrate and washings were combined and concentrated under reduced pressure to yield 14.1 g. of dark oil, which was dissolved in methylene chloride and filtered through 143.5 g. of alumina II (neutral) in a column 60 mm. in width and 65 mm. in length. The eluate was evaporated to 3.28 g. of yellowish solid, which was crystallized first from a mixture of ether-pentane, and then from ether alone to give 1.35 g. of 8-chloro-3-dibenzofuranacetic acid ethyl ester having a melting point of 90°–91°.

EXAMPLE 5

Preparation of 8-chloro-3-dibenzofuranacetic acid

To a solution of 568 mg. of 8-chloro-3-dibenzofuranacetic acid ethyl ester in 40 ml. of hot ethanol was added 10 ml. of 1N sodium hydroxide. The solution was stirred at reflux temperature under an atmosphere of nitrogen for 2 hours and evaporated under reduced pressure. The residue was dried by evaporating three times with benzene and was then digested repeatedly with methylene chloride. The solid was removed by filtration, dried and dissolved in hot water. The hot solution was treated with charcoal and filtered. The filtrate was adjusted to pH 1 with concentrated hydrochloric acid and the mixture cooled. The resulting solid was removed by filtration, dried and crystallized from methanol/ether to give 179 mg. of 8-chloro-3-dibenzofuranacetic acid, having a melting point of 221°–222°.

EXAMPLE 6

Preparation of 2-(8-chloro-3-dibenzofuranyl)ethanol

A solution of 653 mg. of 8-chloro-3-dibenzofuranacetic acid ethyl ester in 75 ml. of ether was added over a 15-minute period, under an atmosphere of nitrogen, to a suspension of 447 mg. of lithium aluminum hydride in 100 ml. of ether. The mixture was stirred at room temperature for 2.5 hours, then at reflux temperature for 8 hours, and finally at room temperature for 10.5 hours, whereupon the reaction mixture was cooled in an ice-water bath, decomposed with 10 ml. of water and stirred cold for 2 hours. Diatomaceous earth and charcoal were added. The solids were removed by filtration and washed with ether. After evaporation of the filtrate and washings, crystallization of the residue twice from methylene chloride-ether-pentane yielded 229 mg. of 2-(8-chloro-3-dibenzofuranyl)ethanol, having a melting point of 115.5°–117°.

EXAMPLE 7

Preparation of 8-chloro-α-methyldibenzofuran-3-acetic acid ethyl ester

To a solution of 16 g. of 2-(4-oxocyclohexyl)propionic acid ethyl ester in 125 ml. of ether, stirred and cooled to −10° C., were added dropwise 4.16 ml. of bromine. The ether solution was washed with two 100 ml. portions of water, 125 ml. of saturated sodium bicarbonate, and three 100 ml. portions of ether. The organic layers were combined, treated with charcoal, dried over anhydrous sodium sulfate, and evaporated at reduced pressure to give 22.6 g. of 2-(3-bromo-4-oxocyclohexyl)propionic acid ethyl ester as a yellow oil.

A mixture comprising 10.42 g. of 4-chlorophenyl, 22.4 g. of anhydrous potassium carbonate and 50 ml. of dimethylformamide was stirred under an atmosphere of nitrogen at reflux temperature for 15–20 minutes, cooled and treated over a period of 45 minutes with a solution of 22.5 g. of 2-(3-bromo-4-oxocyclohexyl)propionic acid ethyl ester in 50 ml. of dimethylformamide. The mixture was stirred at room temperature for 65 hours, at 100° C. for 2 hours, and finally at room temperature for 2.5 hours. The remaining solid was removed by filtration and washed with dimethylformamide. The filtrate was concentrated at 40° C. and reduced pressure, and the residue was partitioned between 500 ml. of ether and 100 ml. of water. The ether layer was washed with 100 ml. of water, three 100 ml. portions of 1 N sodium hydroxide, and two 100 ml. portions of water. The aqueous layers were extracted with two 250 ml. portions of ether, and the combined ether phases were treated with charcoal and dried with anhydrous sodium sulfate. The solids were removed by filtration and the filtrate evaporated at reduced pressure to give 19.7 g. of 2-[3-(4-chlorophenoxy)-4-oxocyclohexyl]-propionic acid ethyl ester as a mixture of geometric isomers, approximate boiling point of 162°–168°/0.4–0.5 mm., in a rotating Buchi kugelrohr.

A mixture of 3.69 g. of distilled 2-[3-(4-chlorophenoxy)-4-oxocyclohexyl]-propionic acid ethyl ester having a boiling point of 167°–168°/0.4 mm. of mercury and 38 g. of polyphosphoric acid was stirred under an atmosphere of nitrogen overnight at room temperature and then for 20 minutes at 80°–85° C. The reaction mass was decomposed with 125 ml. of ice and water, and the resulting mixture was extracted with three 150 ml. portions of ether. The organic layers were washed successively with 100 ml. of water, 100 ml. of 1 N sodium hydroxide, and three 100 ml. portions of water, and dried with anhydrous sodium sulfate (charcoal added). The solids were removed by filtration and the filtrate evaporated to give 2.95 g. of 8-chloro-α-methyl-1,2-dihydro-3(4H)-dibenzofuranacetic acid ethyl ester as a mixture of diastereomers.

A mixture comprising 3.15 g. of distilled 8-chloro-α-methyl-1,2-dihydro-3(4H)-dibenzofuranacetic acid ethyl ester having a boiling point of 146°–147°/0.023 mm. of mercury in a rotating Buchi kugelrohr, 5.22 g. of 2,3-dichloro-5,6-dicyano-1,4-benzoquinone, and 125 ml. of benzene was heated at reflux temperature under an atmosphere of nitrogen for 18 hours, cooled and filtered. The filtrate was evaporated at reduced pressure and the residue dissolved in methylene chloride and filtered through 100 g. of alumina (neutral) in a column 50 mm. in width and 65 mm. in length. The eluate was evaporated to give 2.55 g. of oil which crystallized and had a melting point of 49°–57°. Distillation in a rotating Buchi kugelrohr yielded 2.3 g. of 8-chloro-α-methyl-dibenzofuran-3-acetic acid ethyl ester, having a boiling point of 131°/0.023 mm. of mercury and a melting point of 45°–55.5°.

EXAMPLE 8

Preparation of 8-chloro-α-methyldibenzofuran-3-acetic acid

A mixture comprising 1.78 g. of 8-chloro-α-methyl-dibenzofuran-3-acetic acid ethyl ester, 100 ml. of ethanol and 30 ml. of 1 N sodium hydroxide was stirred at reflux temperature for 2 hours and concentrated at reduced pressure. The residue was dissolved in 125 ml. of hot water and treated with charcoal and diatomaceous earth. The solids were removed by hot filtration and washed with water. The filtrate was stirred and cooled in ice-water while being acidified by the dropwise addition of 5 ml. of concentrated hydrochloric acid. The precipitate was removed by filtration, washed with water and dried to give 1.36 g. of solid. Crystallization from ether-pentane (charcoal and diatomaceous earth added), sublimation at 145°/0.021 mm. of mercury and recrystallization from ether-pentane gave 620 mg. of 8-chloro-α-methyldibenzofuran-3-acetic acid having a melting point (in vacuo) of 159°–162°.

EXAMPLE 9

Preparation of 2-(8-chloro-3-dibenzofuranyl)propanol

To a solution of 977 mg. of 8-chloro-α-methyldibenzofuran-3-acetic acid ethyl ester in 50 ml. of benzene, stirred at room temperature under an atmosphere of nitrogen, was added, over 10 minutes, one ml. of a 70% solution in benzene of sodium bis (2-methoxyethoxy)-aluminum hydride, diluted with 5 ml. of benzene. The mixture was stirred at room temperature for 4.25 hours. During that time, 0.1 ml. portions of the hydride reagent in 5–10 ml. of benzene were added at 0.75 and 1.5 hours. After addition of 5 ml. of acetone and agitation for another 15 minutes, the reaction mixture was decomposed by the gradual addition of 25 ml. of water, and was stirred for an additional 20–25 minutes. The aqueous phase was separated and extracted with three 100 ml. portions of benzene. The organic layers were washed with 25 ml. of saturated sodium bicarbonate, four 25 ml. portions of water and 25 ml. of saturated sodium chloride, dried with anhydrous magnesium sulfate (charcoal and diatomaceous earth added), and evaporated at reduced pressure. The residual oil was distilled in a rotating Buchi kugelrohr to give 604 mg. of 2-(8-chloro-3-dibenzofuranyl)-propanol having a boiling point of 163°–164°/0.4–0.5 mm. of mercury and a melting point of 60°–73°.

EXAMPLE 10

Preparation of 8-chloro-3-dibenzofuranacetamide

A solution of 9.45 g. of 8-chloro-3-dibenzofuranacetic acid in 225 ml. of tetrahydrofuran was treated with 6.01 g. of 98% 1,1'-dicarbonyldiimidazole and stirred overnight (16 hours) at room temperature under an atmosphere of nitrogen. Ammonia was passed into the resultant suspension for 3 hours and stirring continued for an additional 1.5 hours. The solid was removed by filtration and washed with tetrahydrofuran and ether to give 8.14 g. of 8-chloro-3-dibenzofuranacetamide, having a melting point of 258°–263°.

A sample crystallized from aqueous methanol and sublimed at 234°/0.1 mm. of mercury melted at 265.5°–266.5° (in vacuo).

EXAMPLE 11

Preparation of 8-chloro-3-dibenzofuranacetonitrile

To 10 ml. of phosphorous oxychloride, stirred at room temperature under an atmosphere of nitrogen were added 905 mg. of 8-chloro-3-dibenzofuranacetamide in portions over a 15–20 minute period. The suspension was stirred first at room temperature for 45 minutes and then in an ice-water bath for 10 minutes. Thereafter, the suspension was treated with 1.4 ml. of triethylamine, dropwise over a 15–20 minute period. After an additional 15 minutes of stirring cold, the mixture was heated on an oil bath at 90°–100° C. for 2 hours, cooled and concentrated in vacuo. The residue was treated with 25 ml. of water and extracted four times with 75 ml. portions of methylene chloride. The organic layers were washed with three 25 ml. portions of water, dried with anhydrous sodium sulfate and evaporated to dryness. The residue was redissolved in methylene chloride, and the solution filtered through 6.1 g. of alumina II in a column 12 mm. in width and 72 mm. in length. The eluates were evaporated to dryness and the residue crystallized from methylene chloride-ether to give 447 mg. of 8-chloro-3-dibenzofuranacetonitrile, having a melting point of 175°–176°.

EXAMPLE 12

Preparation of 8-chloro-3-dibenzofuranacetic acid 2-dimethylaminoethyl ester hydrochloride A mixture of 1.0 g. of 8-chloro-3-dibenzofuranacetic acid, 1.17 g. of anhydrous potassium carbonate, and 50 ml. of dimethylformamide was stirred for one hour at room temperature, cooled, treated with 1.22 g. of dimethylaminoethyl chloride hydrochloride, and then stirred at room temperature overnight (16 hours). The solid was removed by filtration and the filtrate was concentrated in vacuo below 40° C. The residue was diluted with 100 ml. of water and extracted with three 100 ml. portions of methylene chloride. The organic layers were washed once with 100 ml. of 1 N sodium hydroxide, three times with 100 ml. portions of water, dried over anhydrous magnesium sulfate, and filtered. Concentration of the filtrate at reduced pressure yielded an oil which was dissolved in methanol and acidified with hydrogen chloride. The solution was evaporated to dryness and the residue was dried by azeotropic distillation (three times with benzene and once with methylene chloride). Crystallization from methanol-ether gave 349 mg. of 8-chloro-3-dibenzofuranacetic acid 2-dimethylaminoethyl ester hydrochloride, having a melting point of 201°–202.5° C.

EXAMPLE 13

Preparation of 8-chloro-3-dibenzofuranacetic acid methyl ester

A solution of 1.0 g. of 8-chloro-3-dibenzofuranacetic acid in 100 ml. of methanol, saturated with hydrogen chloride at 0° C., was stirred overnight (16 hours) at room temperature and then heated at reflux temperature for 2 hours. Evaporation of the solvent at reduced pressure and crystallization of the residue from ether-pentane gave 850 mg. of 8-chloro-3-dibenzofuranacetic acid methyl ester, having a melting point of 126.5°–128°.

EXAMPLE 14

Preparation of racemic 8,alpha-dimethyldibenzofuran-3-acetic acid

Sodium p-cresolate, prepared from 8.75 g. of p-cresol and 4.37 g. of sodium methylate, was suspended in 100 ml. of benzene and stirred at room temperature while a solution of 2-(3-bromo-4-oxocyclohexyl)propionic acid ethyl ester in 70 ml. of benzene was added. The resultant mixture was refluxed for 18 hours, cooled and washed successively with two 250 ml. portions of water, two 150 ml. portions of 1 N sodium hydroxide, and two 150 ml. portions of water. The aqueous layers were extracted with two 250 ml. portions of benzene. The combined organic phases were dried with magnesium sulfate and evaporated to give 20.2 g. of oil, which was distilled in a kugelrohr apparatus with an oscillating drive unit to yield 17.6 g. of crude 2-(3-p-cresoxy-4- oxocyclohexyl)propionic acid ethyl ester, b.p. 48°/0.4 mm.

A mixture of 14.8 g. of crude 2-(3-p-cresoxy-4-oxocyclohexyl)propionic acid ethyl ester and 150 g. of polyphosphoric acid was stirred at room temperature for 40 minutes, decomposed by the addition of ice and water, and extracted with three 250 ml. portions of ether. The organic layers were washed successively with two 200 ml. portions of water, two 200 ml. portions of saturated sodium bicarbonate solution, and two 150 ml. portions of water. The combined ether phases were dried with magnesium sulfate and evaporated and the residue distilled twice (kugelrohr apparatus) to give 3.2 g. of crude 8,alpha-dimethyl-1,2-dihydro-3(4H)-dibenzofuranacetic acid ethyl ester, b.p. 95°–120°/0.075 mm.

This material was dissolved in 100 ml. of benzene and heated at reflux temperature for 16 hours with 5.3 g. of 2,3-dichloro-5,6-dicyano-1,4-benzoquinone. The mixture was cooled and the solid removed by filtration and washed with benzene. The dark filtrate was filtered through 35 g. of alumina II and the eluate evaporated to give 2.4 g. of crude 8,alpha-dimethyldibenzofuran-3-acetic acid ethyl ester, m.p. 52°–62° C.

A solution of 2.35 g. of this material in 100 ml. of ethanol was heated at reflux temperature for 2.5 hours in an atmosphere of nitrogen with 50 ml. of 1 N potassium hydroxide and then evaporated. The residue was dissolved in water, treated with charcoal and filtered. The filtrate was acidified with 5–6 ml. of concentrated hydrochloric acid and the resultant precipitate removed by filtration and dissolved in acetone. Evaporation of the acetone solution, removal of water by azeotropic distillation with benzene, and crystallization from ether-pentane gave 1.5 g. of 8,alpha-dimethyldibenzofuran-3-acetic acid, m.p. 151°–153.5° (with sintering at 142°). Sublimation at 132°–140°/0.035–0.065 mm. yielded pure acid as white crystals, m.p. 155°–157° (in vacuo).

EXAMPLE 15

Preparation of racemic 8-amino-alpha-methyldibenzofuran-3-acetic acid ethyl ester hydrochloride A suspension of sodium p-acetamidophenoxide, prepared from 15.1 g. of p-acetamidophenol and 5.4 g. of sodium methylate, in 200 ml. of benzene was stirred at room temperature in an atmosphere of nitrogen while a solution of 2-(3-bromo-4-oxocyclohexyl)propionic acid ethyl ester in 150 ml. of benzene was added dropwise. The mixture was heated at reflux temperature for 50 hours, cooled and washed successively with two 100 ml. portions of water, one 100 ml. portion of saturated sodium bicarbonate solution, and three 50 ml. portions of water. The aqueous phases were extracted with two 250 ml. portions of ethyl acetate, and the combined organic layers were dried with sodium sulfate and evaporated to give 32.65 g. of oil, which was dissolved in methylene chloride and filtered through 250 g. of alumina II. Evaporation of the eluates yielded 24 g. of crude 2-[3-(4-acetamidophenoxy)-4-oxcyclohexyl]propionic acid ethyl ester.

A mixture of 23 g. of this material and 230 g. of polyphosphoric acid was stirred vigorously for 30 minutes at room temperature, decomposed with ice and water, and extracted thrice with ether (total volume of 1 liter). The organic layers were washed successively with one 250 ml. portion of water, two 100 ml. portions of 1 N sodium hydroxide, and four 100 ml. portions of water, dried with sodium sulfate, and evaporated to give 12.8 g. of oil which was crystallized once from methylene chloride-ether-pentane and twice from methylene chloride-ether to yield 1.45 g. of 8-acetamido-alpha-methyl-1,2-dihydro-3(4H)-dibenzofuranacetic acid ethyl ester, m.p. 140.5°–143° (in vacuo).

The first crystallization mother liquor from the preceding step was evaporated and 7.7 g. of the semicrystalline residue was dissolved in 200 ml. of benzene, mixed with 11.2 g. of 2,3-dichloro-5,6-dicyano-1,4-benzoquinone and heated at reflux temperature with a Dean-Stark trap for 17 hours in an atmosphere of nitrogen. The cooled mixture was filtered and the residue washed with benzene and methylene chloride. The dark filtrate was evaporated and the residue chromatographed on 152 g. of alumina II in a column 40 mm. wide and 180 mm. long eluting successively with benzene, methylene chloride, ethyl acetate and acetone. The methylene chloride eluate was evaporated to give 1.58 g. of brown gum which was dissolved in 200 ml. of ethanol saturated at 0° C. with hydrogen chloride. The solution was stirred at 0° for one hour, heated at reflux temperature for 2 hours, and permitted to stand at room temperature for 15 hours. Evaporation of the solvent and drying of the residue by azeotropic distillation with benzene gave 1.45 g. of solid which was crystallized first from ethanol-ether and then from methanol-ether to yield 718 mg. of 8-amino-alpha-methyldibenzofuran-3-acetic acid ethyl ester hydrochloride; white crystals, m.p. 192°–193° (in vacuo).

EXAMPLE 16

Preparation of 8-chloro-alpha-methyldibenzofuran-3-acetamide

A solution of 2.75 g. of 8-chloro-alpha-methyldibenzofuran-3-acetic acid in 100 ml. of tetrahydrofuran was stirred for 16 hours at room temperature in an atmosphere of nitrogen with 1.66 g. of 1,1'-carbonyldiimidazole, cooled in an ice-water bath and saturated with ammonia. Evaporation of the mixture gave 4.32 g. of solid which was digested several times with boiling ether. The insoluble material obtained by filtration was crystallized from tetrahydrofuran-ether to yield 1.63 g. of white crystalline 8-chloro-alpha-methyldibenzofuran-3-acetamide, m.p. 210°–211°.

EXAMPLE 17

Preparation of 8-chloro-alpha-methyl-3-dibenzofuranacetic acid 2-dimethylaminoethyl ester hydrochloride A solution of 1.1 g. of 8-chloro-alpha-methyldibenzofuran-3-acetic acid in 25 ml. of dimethylformamide was stirred for 1 hour and 25 minutes at room temperature in an atmosphere of nitrogen with 1.22 g. of anhydrous potassium carbonate and then treated over a 10–12 minute period with a suspension of 2-chloro-N,N-dimethylethylamine hydrochloride in 10 ml. of dimethylformamide. The mixture was stirred first at room temperature for 69 hours and then at 100° for 1 hour, cooled, poured onto 100 g. of ice, diluted with water and extracted with three 200 ml. portions of methylene chloride. The organic layers were washed with two 150 ml. portions of water, dried with sodium sulfate and evaporated to give 1.7 g. of oil, which was dissolved in methanol and acidified with 4.17 N ethanolic hydrogen chloride. Evaporation of the solvents and crystallization of the residue twice from methanol-ether gave 953 mg. of 8-chloro-alpha-methyl-3-dibenzofuranacetic acid 2-dimethylaminoethyl ester hydrochloride hemihydrate; white crystals, m.p. 178°–183° (in vacuo, unsharp, variable).

Anhydrous 8-chloro-alpha-methyl-3-dibenzofuranacetic acid 2-dimethylaminoethyl ester hydrochloride was obtained by drying at 105° C./0.1 mm for 16 hours; white crystals, m.p. 177°–182°.

EXAMPLE 18

Preparation of 8-fluoro-alpha-methyldibenzofuran-3-acetic acid

To a suspension of sodium 4-fluorophenoxide, prepared from 11.2 g. of 4-fluorophenol and 5.4 g. of sodium methylate, in 100 ml. of benzene, was added gradually a solution of 27.7 g. of 2-(3-bromo-4-oxocyclohexyl)propionic acid ethyl ester in about 25 ml. of benzene. The mixture was stirred for 16 hours, at room temperature and one hour at reflux temperature and was cooled and washed successively with two 100 ml. portions of water, one 100 ml. portion of 1 N sodium hydroxide, and three 100 ml. portions of water. The aqueous layers were extracted with two 150 ml. portions of benzene, and the combined organic phases were dried with magnesium sulfate and evaporated. The residual oil was distilled in a kugelrohr apparatus to give 9.75 g. of 2-[3-(4-fluorophenoxy)-4-oxocyclohexyl]propionic acid ethyl ester, b.p. 120°–140°/0.05 mm.

A mixture of this material and 140 g. of polyphosphoric acid was stirred at room temperature for 10 minutes, decomposed with ice and water, and extracted with three 250 ml. portions of ether. The organic layers were washed successively with one 150 ml. portion of water, one 150 ml. portion of 1 N sodium hydroxide, and three 150 ml. portions of water, dried with magnesium sulfate, and evaporated to give 7.8 g. of 8-fluoro-alpha-methyl-1,2-dihydro-3(4H)-dibenzofuranacetic acid ethyl ester.

A solution of this material in 200 ml. of benzene was heated for 16 hours at reflux temperature with 12.8 g. of 2,3-dichloro-5,6-dicyano-1,4-benzoquinone, cooled and filtered. The filtrate was washed once with water, once with 1 N sodium hydroxide, and three times with saturated sodium chloride solution, dried with magnesium sulfate and evaporated. The residue was applied to 60 g. of alumina II and eluted successively with benzene, methylene chloride, ethyl acetate and acetone. Evaporation of the benzene eluate yielded 4.6 g. of 8-fluoro-alpha-methyldibenzofuran-3-acetic acid ethyl ester.

A solution of 208 mg. of 8-fluoro-alpha-methyldibenzofuran-3-acetic acid ethyl ester in 100 ml. of ethanol was heated at reflux temperature for 2.5–3 hours in an atmosphere of nitrogen with 10 ml. of 1 N sodium hydroxide and evaporated at diminished pressure. The residue was dissolved in hot water and the solution treated with charcoal and Celite and filtered. Acidification of the filtrate with concentrated hydrochloric acid yielded a precipitate which was removed by filtration, washed with water and dissolved in acetone. This solution was evaporated and the residue was dried by azeotropic distillation with benzene and sublimed at 135°–145° C./0.02 mm. The sublimate was crystallized twice from ether-pentane to give 28 mg. of white, crystalline 8-fluoro-alpha-methyldibenzofuran-3-acetic acid, m.p. 153°–155° (in vacuo).

EXAMPLE 19

Preparation of (−)-8-chloro-alpha-methyldibenzofuran-3-acetic acid (+)-alphamethylbenzylamine salt A hot solution of 5.49 g. of racemic 8-chloro-alpha-methyldibenzofuran-3-acetic acid in 30 ml. of ethanol and 30 ml. of acetonitrile was treated with 2.58 ml. of d-(+)-alpha-methylbenzylamine and permitted to stand for 2 hours at room temperature. The precipitate was removed by filtration and washed with acetonitrile and ether to give 6.54 g. of white solid, m.p. 172°–180° dec., $\alpha_D^{25.4°} = +4.3°$ (c=0.98%, methanol), which was crystallized successively from ethanol-acetonitrile, methanol-acetonitrile and ethanol (six times) to yield 574 mg. of white, crystalline (−)-8-chloro-alpha-methyldibenzofuran-3-acetic acid (+)-alpha-methylbenzylamine salt, m.p. 184°–185°; $\alpha_D^{25.4°} = +14.2°$ (c=0.99%, methanol).

EXAMPLE 20

Preparation of (−)-8-chloro-alpha-methyldibenzofuran-3-acetic acid

A mixture of 503 mg. of (−)-8-chloro-alpha-methyldibenzofuran-3-acetic acid (+)-alpha-methylbenzylamine salt and 5 ml. of 1 N sodium hydroxide was stirred until a clear solution formed. Dilution with 10 ml. of water and acidification by dropwise addition of 1 ml. of concentrated hydrochloric acid yielded a precipitate which was removed by filtration, washed with water and dissolved in acetone. Evaporation of the solvent and crystallization of the residue from ether-pentane and then from methylene chloride-ether-pentane gave 236 mg. of white, crystalline (−)-8-chloro-alpha-methyldibenzofuran-3-acetic acid, m.p. 156°–157° (in vacuo); $\alpha_D^{25.1°} = -44.4°$ (c=0.99%, methanol).

EXAMPLE 21

Preparation of (+)-8-chloro-alpha-methyldibenzofuran-3-acetic acid (−)-alpha-methylbenzylamine salt The reaction mother liquor and the first three recrystallization mother liquors from the preparation of (−)-8-chloro-alpha-methyldibenzofuran-3-acetic acid (+)-alpha-methylbenzylamine salt were combined and evaporated to give 3.27 g. of residue which was treated with 25 ml. of 1 N sodium hydroxide, diluted with water, warmed with charcoal and filtered. The clear filtrate was acidified with concentrated hydrochloric acid and the resultant precipitate removed by filtration, washed with water and dissolved in acetone. Evaporation of the organic solvent and drying of the residue by azeotropic distillation with benzene gave 3.17 g. of crude acid, which was dissolved in 125 ml. of hot ethanol and treated with 1.5 ml. of 1-(−)-alpha-methylbenzylamine. The resultant mixture was stirred at room temperature and the precipitate by filtration and washed with cold ethanol to yield 2.36 g. of off-white solid, m.p. 173°–182°; $\alpha_D^{25.4°} = -8.8°$ (c=0.99%, methanol). Six crystallizations from ethanol gave 642 mg. of white, crystalline (+)-8-chloro-alpha-methyldibenzofuran-3-acetic acid (−)-alpha-methylbenzylamine salt, m.p. 179°–180.5°; $\alpha_D^{25°} = -14.2°$ (c=1.0%, methanol).

EXAMPLE 22

Preparation of (+)-8-chloro-alpha-methyldibenzofuran-3-acetic acid

A solution of 600 mg. of (+)-8-chloro-alpha-methyl-dibenzofuran-3-acetic acid (−)-alpha-methylbenzylamine salt in 6 ml. of 1 N sodium hydroxide was diluted with 15 ml. of water, acidified with 1 ml. of concentrated hydrochloric acid and stirred for 1 hour at room temperature. The precipitate was removed by filtration, washed with water and dissolved in acetone. Evaporation of this solution and drying of the residue by azeotropic distillation with benzene yielded a solid which was crystallized twice from ether-pentane to give 253 mg. of white, crystalline (+)-8-chloro-alpha-methyl-dibenzofuran-3-acetic acid, m.p. 155°–157° (in vacuo); $a_D{}^{25.1°} = -43.7°$ (c=1.0%, methanol).

EXAMPLE 23

Preparation of 3-(8-chloro-3-dibenzofuranyl)propionic acid ethyl ester

A solution of 16.8 g. of 3-(4-oxocyclohexyl)propionic acid ethyl ester in 200 ml. of ether was stirred at −20° C. during the dropwise addition, over a ten minute period, of 4.36 ml. of bromine. It was then stirred an additional 40 minutes at room temperature and was washed successively with three 100 ml. portions of water, one 100 ml. portion of saturated sodium bicarbonate solution and three 100 ml. portions of water. The aqueous phases were extracted with two 100 ml. portions of ether, and the combined ether layers were dried and magnesium sulfate and evaporated to give 23.6 g. of 3-(3-bromo-4-oxocyclohexyl)propionic acid ethyl ester.

A mixture of 10.9 g. of 4-chlorophenol, 23.6 g. of anhydrous potassium carbonate, and 45 ml. of dimethylformamide was stirred for 16 hours at room temperature and for 15 minutes at 100° C., cooled, and treated with a solution of 23.6 g. of 3-(3-bromo-4-oxocyclohexyl)propionic acid ethyl ester in 45 ml. of dimethylformamide over a period of 1.25 hours. The resultant suspension was heated at 100° C. for 1.5 hours, stirred at room temperature for 16 hours and filtered. The filtrate was evaporated at diminished pressure below 40° C. and the residue mixed with 200 ml. of water and extracted with three 200 ml. portions of ether. The ether phases were washed successively with one 200 ml. portion of water, three 100 ml. portions of 1 N sodium hydroxide and three 200 ml. portions of water, dried with magnesium sulfate and evaporated to give 19 g. of 3-[3-(4-chlorophenoxy)-4-oxocyclohexyl]propionic acid ethyl ester.

A mixture of 15.8 g. of 3-[3-(4-chlorophenoxy)-4-oxocyclohexyl]propionic acid ethyl ester and 162 g. of polyphosphoric acid was stirred at room temperature for 65 minutes and then at 85°–90° C. for ten minutes, decomposed with ice and water, and extracted three times with a total volume of 1 liter of ether. The organic layers were washed successively with one 150 ml. portion of water, one 100 ml. portion of 1 N sodium hydroxide and four 150 ml. portions of water, dried with sodium sulfate and evaporated to an oily residue, which was dissolved in methylene chloride and filtered through 115 g. of alumina II. Evaporation of the eluate yielded 10.1 g. of 3-[8-chloro-1,2-dihydro-3(4H)-dibenzofuranyl]propionic acid ethyl ester.

A solution of 3.07 g. of 3-[8-chloro-1,2-dihydro-3(4H)-dibenzofuranyl]propionic acid ethyl ester in 250 ml. of benzene was heated at reflux temperature in an atmosphere of nitrogen during the addition, over a half hour period, of a suspension of 4.8 g. of 2,3-dichloro-5,6-dicyano-1,4-benzoquinone in 300 ml. of benzene. Thereafter, the mixture was heated at reflux temperature for an additional 66 hours and cooled, and the solid removed by filtration and washed with benzene. Evaporation of the filtrate yielded a semi-solid which was dissolved in methylene chloride and filtered through 56.5 g. of alumina II. Evaporation of the eluates gave a brown oil which was dissolved in 150 ml. of ether and washed successively with one 50 ml. portion of 1 N sodium hydroxide and four 50 ml. portions of water. The aqueous layers were extracted with two 150 ml. portions of ether, and the combined ether phases were dried with sodium sulfate and evaporated to give 2.02 g. of oil, which was distilled twice in a kugelrohr apparatus to yield 832 mg. of 3-(8-chloro-3-dibenzofuranyl)-propionic acid ethyl ester, b.p. 176°–181°/0.15 mm.

EXAMPLE 24

Preparation of 3-(8-chloro-3-dibenzofuranyl)propionic acid

A solution of 1.05 g. of 3-(8-chloro-3-dibenzofuranyl)propionic acid ethyl ester in 50 ml. of ethanol was heated at reflux temperature for 1 hour with 25 ml. of 1 N sodium hydroxide and then concentrated at diminished pressure. The residual suspension was diluted with water, treated with 10 ml. of concentrated hydrochloric acid and stirred for 16 hours at room temperature. The solid was removed by filtration, washed with water and dissolved in tetrahydrofuran. Evaporation and drying of the residue by azeotropic distillation with benzene gave a solid which was crystallized from acetone-methylene chloride-ether and sublimed at 160°/0.15 mm. to yield white, crystalline 3-(8-chloro-3-dibenzofuranyl)propionic acid, m.p. 174°–178°.

EXAMPLE 25

| Tablet Formulation | Per Tablet |
|---|---|
| Racemic 8-chloro-α-methyldibenzofuran-3-acetic acid | 25 mg. |
| Dicalcium Phosphate Dihydrate, Unmilled | 175 mg. |
| Corn Starch | 24 mg. |
| Magnesium Stearate | 1 mg. |
| Total Weight | 225 mg. |

Procedure:
1. 25 Parts of racemic 8-chloro-α-methyldibenzofuran-3-acetic acid and 24 parts of corn starch are mixed together and passed through a No. 00 screen in Model "J" Fitzmill with hammers forward.
2. This premix is then mixed with 175 parts of dicalcium phosphate and one-half of a part of the magnesium stearate, and passed through a No. 1A screen in Model "J" Fitzmill with knives forward, and slugged.
3. The slugs are passed through a No. 2A plate in a Model "D" Fitzmill at slow speed with knives forward, and the other one-half of a part magnesium stearate is added.
4. The mixture is mixed and compressed.

EXAMPLE 26

| Capsule Formulation | Per Capsule |
|---|---|
| Racemic 8-chloro-α-methyldibenzofuran-3-acetic acid | 50 mg. |
| Lactose, U.S.P. | 125 mg. |
| Corn Starch, U.S.P. | 30 mg. |
| Talc, U.S.P. | 5 mg. |
| Total Weight | 210 mg. |

Procedure:
1. 50 Parts of 8-chloro-α-methyldibenzofuran-3-acetic acid is mixed with 125 parts of lactose and 30 parts of corn starch in a suitable mixer.
2. The mixture is further blended by passing through a Fitzpatrick Comminuting Machine with a No. 1A screen with knives forward.
3. The blended powder is returned to the mixer, 5 parts talc are added and blended thoroughly.
4. The mixture is filled into No. 4 hard shell gelatin capsules on a Parke Davis capsulating machine.

EXAMPLE 27

| Tablet Formulation | Per Tablet |
|---|---|
| Racemic 8-chloro-α-methyldibenzofuran-3-acetic acid | 100 mg. |
| Lactose, U.S.P. | 202 mg. |
| Corn Starch, U.S.P. | 80 mg. |
| Amijel BO11[1] | 20 mg. |
| Calcium Stearate | 8 mg. |
| Total Weight | 410 mg. |

Procedure:
1. 100 Parts of 8-chloro-α-methyldibenzofuran-3-acetic acid, 202 parts of lactose, 80 parts of corn starch, and 20 parts Amijel BO11 are blended in a suitable mixer.
2. The mixture is granulated to a heavy paste with water and the moist mass is passed through a No. 12 screen. It is then dried overnight at 110° F.
3. The dried granules are passed through a No. 16 screen and transferred to a suitable mixer. The calcium stearate is added and mixed until uniform.
4. The mixture is compressed at a tablet weight of 410 mg. using tablet punches having a diameter of approximately ⅜". (Tablets may be either flat or biconvex and may be scored if desired.)

[1] A prehydrolyzed food grade corn starch. Any similar prehydrolyzed corn starch may be used.

EXAMPLE 28

| Suppository Formulation | Per 1.3 Gm. Suppository |
|---|---|
| Racemic 8-chloro-α-methyldibenzofuran-3-acetic acid | 0.025 mg. |
| Hydrogenated coconut oil | 1.230 mg. |
| Carnauba Wax | 0.045 gm. |

Procedure:
1. 123 Parts of hydrogenated coconut oil and 4.5 parts of carnauba wax are melted in a suitable size glass-lined container (stainless steel may also be used), mixed well and cooled to 45° C.
2. 2.5 Parts of racemic 8-chloro-α-methyldibenzofuran-3-acetic acid, which has been reduced to a fine powder with no lumps, is added and stirred until completely and uniformly dispersed.
3. The mixture is poured into suppository molds to yield suppositories having an individual weight of 1.3 gms.
4. The suppositories are cooled and removed from molds, and individually wrapped in wax paper for packaging. (Foil may also be used.)

We claim:
1. A compound of the formula

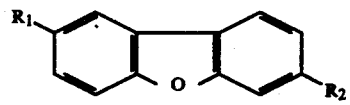

wherein $R_1$ is halogen; $R_2$ is

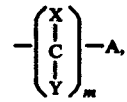

wherein A is hydroxy; X and Y, independently, are hydrogen or lower alkyl, and m is 1 to 7; or when X and Y are different, its enantiomers.

2. A compound of the formula

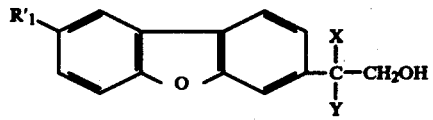

wherein $R_1'$ is halogen, and X and Y, independently, are hydrogen or lower alkyl, or, when X and Y are different, enantiomers.

3. A compound in accordance with claim 2, wherein $R_1'$ is chlorine.

4. A compound in accordance with claim 3, i.e., racemic 2-(8-chloro-3-dibenzofuranyl)propanol.

5. A compound in accordance with claim 4, i.e., 2-(8-chloro-3-dibenzofuranyl)ethanol.

* * * * *